(12) United States Patent
Ponomarenko et al.

(10) Patent No.: US 7,717,895 B2
(45) Date of Patent: May 18, 2010

(54) METHOD FOR APPLICATION OF DISPOSABLE ABSORBENT ARTICLES AND PROVIDING A KIT OF A PACKAGE AND DISPOSABLE ABSORBENT ARTICLE

(75) Inventors: Ekaterina Anatolyevna Ponomarenko, Bad Soden (DE); Cornelia Beate Martynus, Nidderau-Ostheim (DE); Kara Marie Cain, Cincinnati, OH (US); Sarah Innes, Toronto (CA); Ekow Mensah, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 196 days.

(21) Appl. No.: 11/873,867

(22) Filed: Oct. 17, 2007

(65) Prior Publication Data
US 2008/0087569 A1    Apr. 17, 2008

Related U.S. Application Data

(60) Provisional application No. 60/852,189, filed on Oct. 17, 2006.

(51) Int. Cl.
*A61F 13/15* (2006.01)
*B65D 73/00* (2006.01)

(52) U.S. Cl. ............... 604/385.24; 206/440; 206/459.5; 206/494; 604/385.01; 604/385.23

(58) Field of Classification Search .............. 206/459.5, 206/494, 440; 604/385.01, 385.02, 386, 604/385.19, 385.23, 385.24
See application file for complete search history.

(56) References Cited

U.S. PATENT DOCUMENTS

| | | |
|---|---|---|
| 3,848,594 A | 11/1974 | Buell |
| 3,860,003 A | 1/1975 | Buell |
| 4,515,595 A | 5/1985 | Kievit et al. |
| 4,610,678 A | 9/1986 | Weisman et al. |
| 4,662,875 A | 5/1987 | Hirotsu et al. |
| 4,673,402 A | 6/1987 | Weisman et al. |
| 4,695,278 A | 9/1987 | Lawson |
| 4,710,189 A | 12/1987 | Lash |

(Continued)

FOREIGN PATENT DOCUMENTS

EP    1 201 212 A    5/2002

(Continued)

OTHER PUBLICATIONS

PCT International Search Report, mailed Feb. 19, 2008, 3 pages.

*Primary Examiner*—Bryon P Gehman
(74) *Attorney, Agent, or Firm*—Richard L. Alexander; William E. Gallagher (57) ABSTRACT

A method for accomplishing the application to a wearer of a disposable absorbent article having particular features is disclosed. The method includes the step of providing a kit, the kit including a disposable absorbent article having an elastically stretchable topsheet with a longitudinal opening therethrough and a primary serviceable indicium disposed thereon, and a package having secondary information including a depiction of at least part of the absorbent article and the primary serviceable indicium, the primary serviceable indicium and the secondary information being present to aid the care giver in the correct application of the article to a wearer.

12 Claims, 6 Drawing Sheets

U.S. PATENT DOCUMENTS

| | | |
|---|---|---|
| 4,795,454 A | 1/1989 | Dragoo |
| 4,808,178 A | 2/1989 | Aziz et al. |
| 4,816,025 A | 3/1989 | Foreman |
| 4,834,735 A | 5/1989 | Alemany et al. |
| 4,846,815 A | 7/1989 | Scripps |
| 4,888,231 A | 12/1989 | Angstadt |
| 4,892,536 A | 1/1990 | Desmarais et al. |
| 4,894,060 A | 1/1990 | Nestegard |
| 4,909,803 A | 3/1990 | Aziz et al. |
| 4,946,527 A | 8/1990 | Battrell |
| 4,963,140 A | 10/1990 | Robertson et al. |
| 4,965,122 A | 10/1990 | Morman |
| 4,981,747 A | 1/1991 | Morman |
| 4,990,147 A | 2/1991 | Freeland |
| 5,026,364 A | 6/1991 | Robertson |
| 5,037,416 A | 8/1991 | Allen et al. |
| 5,114,781 A | 5/1992 | Morman |
| 5,116,662 A | 5/1992 | Morman |
| 5,137,537 A | 8/1992 | Herron et al. |
| 5,147,345 A | 9/1992 | Young et al. |
| 5,151,092 A | 9/1992 | Buell et al. |
| 5,156,793 A | 10/1992 | Buell et al. |
| 5,167,897 A | 12/1992 | Weber et al. |
| 5,221,274 A | 6/1993 | Buell et al. |
| 5,226,992 A | 7/1993 | Morman |
| 5,260,345 A | 11/1993 | Desmarais et al. |
| 5,269,775 A | 12/1993 | Freeland et al. |
| 5,336,545 A | 8/1994 | Morman |
| 5,342,338 A | 8/1994 | Roe |
| 5,387,207 A | 2/1995 | Dyer et al. |
| 5,397,316 A | 3/1995 | Lavon et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| 5,607,760 A | 3/1997 | Roe |
| 5,609,587 A | 3/1997 | Roe |
| 5,625,222 A | 4/1997 | Yoneda et al. |
| 5,635,191 A | 6/1997 | Roe et al. |
| 5,643,588 A | 7/1997 | Roe et al. |
| 5,725,382 A * | 3/1998 | Walter et al. .............. 206/459.5 |
| 5,865,823 A | 2/1999 | Curro |
| 6,004,306 A | 12/1999 | Robles et al. |
| 6,107,537 A | 8/2000 | Elder et al. |
| 6,120,487 A | 9/2000 | Ashton |
| 6,702,795 B2 * | 3/2004 | Klemp ................... 604/385.24 |
| 7,223,261 B2 * | 5/2007 | Mueller et al. ......... 604/385.01 |
| 7,273,476 B2 * | 9/2007 | Mueller et al. ......... 604/385.24 |
| 7,597,689 B2 * | 10/2009 | Hoffmann et al. ...... 604/385.01 |
| 2003/0088224 A1 * | 5/2003 | Ceman et al. .......... 604/385.01 |
| 2003/0158532 A1 | 8/2003 | Magee et al. |
| 2004/0092902 A1 | 5/2004 | Hoffman et al. |
| 2005/0288644 A1 * | 12/2005 | Mizutani et al. ....... 604/385.02 |
| 2006/0004337 A1 * | 1/2006 | Datta .................... 604/385.01 |
| 2006/0212010 A1 * | 9/2006 | Roe et al. .............. 604/385.01 |
| 2007/0032766 A1 | 2/2007 | Liu et al. |

FOREIGN PATENT DOCUMENTS

| | | |
|---|---|---|
| EP | 1 287 799 A2 | 3/2003 |
| EP | 0 937 446 B1 | 9/2004 |
| EP | 1 279 357 B1 | 9/2005 |
| WO | WO-95/16746 A1 | 6/1995 |
| WO | WO02/091968 A2 | 11/2002 |
| WO | WO2005/041834 A1 | 5/2005 |
| WO | WO2005/102239 A1 | 11/2005 |

* cited by examiner

METHOD FOR APPLICATION OF DISPOSABLE ABSORBENT ARTICLES AND PROVIDING A KIT OF A PACKAGE AND DISPOSABLE ABSORBENT ARTICLE

CROSS REFERENCE TO RELATED APPLICATION

This application claims the benefit of U.S. Provisional Application No. 60/852,189, filed Oct. 17, 2006, the substance of which is incorporated herein by reference.

FIELD OF THE INVENTION

The present invention relates to a kit of one or more disposable absorbent articles and a package, and in another embodiment to a package suitable for disposable absorbent articles, said package comprising secondary information, conveying to the wearer or caregiver how to apply the article and showing said article, and said article of the kit and shown on the package comprising at least primary serviceable indicium to aid the wearer or caregiver with the application of said article and to ensure proper use and optimal performance of the article.

BACKGROUND OF THE INVENTION

Many disposable articles such as diapers and adult incontinence products comprise elasticated, stretchable components, which provide stretch in the longitudinal direction, such as leg cuffs and barrier cuffs. Another example is a diaper with a topsheet with a large opening that can receive feces and pass it to avoid space underneath the topsheet.

The inventors have found that in particular when the elasticated components are such that they can contract the article significantly, application of such absorbent articles can be difficult. They also found that when the elastic forces of such components are very strong, it may be difficult to fully stretch the article while at the same time trying to position it, and/or that a stretched article often folds up or contracts into a less stretched state. They also found that the article is often stretched incorrectly or incompletely or that the elastic components, or the whole article, are applied incorrectly. This may lead in use to leakage and discomfort.

Co-pending application EP1279357 proposes the use of an application aid that helps to fix the article in place during application and thus facilitates the application by the caregiver. However, such an aid may add complexity for the caregiver, and it does still not guarantee correct application of the article and avoidance of leakage or discomfort.

The inventors have now found that when the package of such highly stretchable articles comprise an indication how to stretch the stretchable article and/or how to align the article, e.g. with the genitals and anus of the user, and that when the absorbent articles also comprise a serviceable indicium conveying this information, and that when this serviceable indicium is also included in the secondary information comprised by the package, that then the wearer or care giver will apply the article correctly and the article will be comfortable to wear and it will perform optimally. Because the information of the package also shows the disposable absorbent article and the serviceable indicium thereof, the wearer or caregiver can re-apply the instructions of the package and apply the article correctly, i.e. stretch the article correctly and/or align the article correctly with for example the genitals and/or anus.

SUMMARY OF THE INVENTION

An embodiment of the invention relates to a disposable absorbent article-kit comprising a package and at least one disposable absorbent article comprising a stretchable component selected from the group consisting of a stretchable topsheet, stretchable backsheet, stretchable absorbent core and/or stretchable cuffs, wherein the disposable absorbent article comprises at least one primary serviceable indicium conveying to the care giver or user that a pulling force is to be applied by the caretaker or wearer to the absorbent article for correct application of the absorbent article to the wearer; and/or how to align the article with the genitals and anus of the wearer. The package comprises secondary information either: depicting the absorbent article and the primary serviceable indicium or part thereof, and instructing the wearer or caregiver to apply a pulling force to the absorbent article) by the wearer or caregiver for correct application of the absorbent article to the wearer; and/or depicting the absorbent article and the primary serviceable indicium or part thereof, and informing the wearer or caregiver how to align the genitals and/or anus of the wearer with the primary serviceable indicium.

Another embodiment of the invention relates to a package suitable for containing at least one disposable absorbent article to be worn around the lower torso, the package comprising secondary information conveying to the wearer or caregiver to apply a pulling force by the wearer or caregiver to the absorbent article comprising a primary serviceable indicium that is visible or partially visible on the package, for correct application of the absorbent article to the wearer; and/or conveying to the wearer or caregiver how to align the genitals and/or anus of the wearer with the primary serviceable indicium, and wherein the secondary information depict the disposable absorbent article and the primary serviceable indicium.

DETAILED DESCRIPTION OF THE INVENTION

Disposable Absorbent Article (1)

The disposable absorbent articles (1) herein may be worn by a wearer around the lower torso. Said articles (1) may include diapers (herein also referred to with (1)), including training or pull-on pants, and adult incontinence articles, and said articles (1) may be diapers or adult incontinence articles with fasteners that allow fastening around the torso of the wearer, as shown in for example FIGS. 1-4.

The articles (1) herein may comprise a stretchable component selected from the group consisting of a stretchable topsheet (2), stretchable backsheet (4), stretchable absorbent core (3), and/or stretchable cuff, including an anal cuff, a leg cuffs and/or barrier cuffs.

The stretchable component may stretch at least about 140%, at least about 160% or at least about 180% or even at least about 200%. The stretchable component may be elastic or elasticated and it can stretch as above, and it may contract, after fully stretching it once, to about 120% or less of its original size. The stretchable and elastic(ated) component may provide the article (1) with stretch and elasticity in substantially the longitudinal direction (parallel or along the Y-axis).

In one embodiment, the article (1) may comprise one or more elasticated leg cuffs and/or one or more elasticated barrier cuffs. Each such pair may comprise two cuffs that are positioned along and/or in proximity to either longitudinal side of the article (1), typically extending in longitudinal direction. The elasticated cuffs may oppose one another and they may be mirror images of one another in the y-axis. Such cuffs may for example be attached to the backsheet (4), topsheet or core (3). They may be capable of obtaining a configuration out of plane of the topsheet, core (3) and/or backsheet (4), for example perpendicular thereto. Leg cuffs may also be referred to as leg bands, side flaps, or elastic cuffs, as described in; U.S. Pat. No. 3,860,003; U.S. Pat. Nos. 4,808, 178 and 4,909; U.S. Pat. Nos. 4,695,278 and 4,795,454.

In one embodiment, the disposable absorbent article (1) may comprise a stretchable topsheet (2), formed from one or more sheets or one or more laminated sheet, comprising typically an elastic material, for example an elastic sheet and/or at least one elastic band or strand. It may comprise at least a pair of opposing elastic bands or strands, that are mirror images of one another in the Y-axis. The elasticated topsheet (2) may have elasticity in the longitudinal direction of the article (1). The topsheet (2) may comprise at least one opening (5) that is large enough to receive feces and allow it to pass to a void space underneath said topsheet (2). A single opening (5) for the reception of fecal material may be preferred. The opening (5) may be in the form of a slit opening (5). The opening (5) may be present in (part of) the front region (20) of the topsheet (2) (in use towards the front of the user) and in (part of) the back region (24) of the topsheet (2). The topsheet (2) may have a slit opening (5), which has a longitudinal dimension (length) substantially parallel to the longitudinal axis of the topsheet (2) and of the diaper (1). The topsheet (2) may be present over the whole length of the absorbent core (3). Diapers (1) are shown in FIGS. 1-4. The topsheet (2) may be a unitary sheet or laminated sheet, with optionally attached thereto the genital coversheet (6) described below and shown in the Figures.

In stretched state the opening (5) (or openings) of the topsheet (2) may be configured such that from (in fully, flat stretched state) about 20% to about 40%, or from about 20% to about 30% of the length of the opening (5) (or total length of the openings) extends from the transverse axis of the topsheet (2) towards the front edge (25) of the topsheet (2), and the remaining percentage extends towards the back edge (26) of the topsheet (2).

The dimensions and exact shape of the opening (5) may vary, depending on the size of the topsheet (2) and/or the absorbent article (1). For example, in one embodiment the opening (5) may be in the form of a slit opening (5) with substantially parallel longitudinal side edges (31), which may be connected in the front and back by V-shaped or rounded V-shaped (as shown herein after) front and back edges.

The maximum length of the slit opening (5) may be for example (in fully stretched, flat state) about 40% to about 90% or about 50% to about 80%, or about 60% to about 70%, of the total length L of the absorbent article (1).

The average width of the opening (5) herein, in fully stretched flat state, may be from about 5% to about 30%, or about 10% to about 25%, of the average width of the topsheet (2) (including opening (5) width).

In one embodiment of the invention, relating to an absorbent article (1) with a topsheet (2) with one or more openings, as referred to above, the absorbent article (1) may also comprise a genital coversheet (6) that is present under, in or above the opening (5) in the topsheet (2), typically only that part of the opening (5) that is in close proximity with the genitals during use, i.e. the front region (20) of the opening (5). The maximum length of the part of the genital coversheet present above, in or under the opening (5) genital coversheet may be (in fully stretched flat state) about 10% to about 50% of the maximum length of the opening (5), or about 10% to about 30%, or about 13% to about 28% or about 17% to about 27%. In other words, at the most about 50% of the maximum length of the opening (5) may be 'covered' by the longest part of the genital coversheet (6), but at least about 10% of the maximum length of the opening (5) may be covered by the longest part of the genital coversheet (6).

Figure 4:
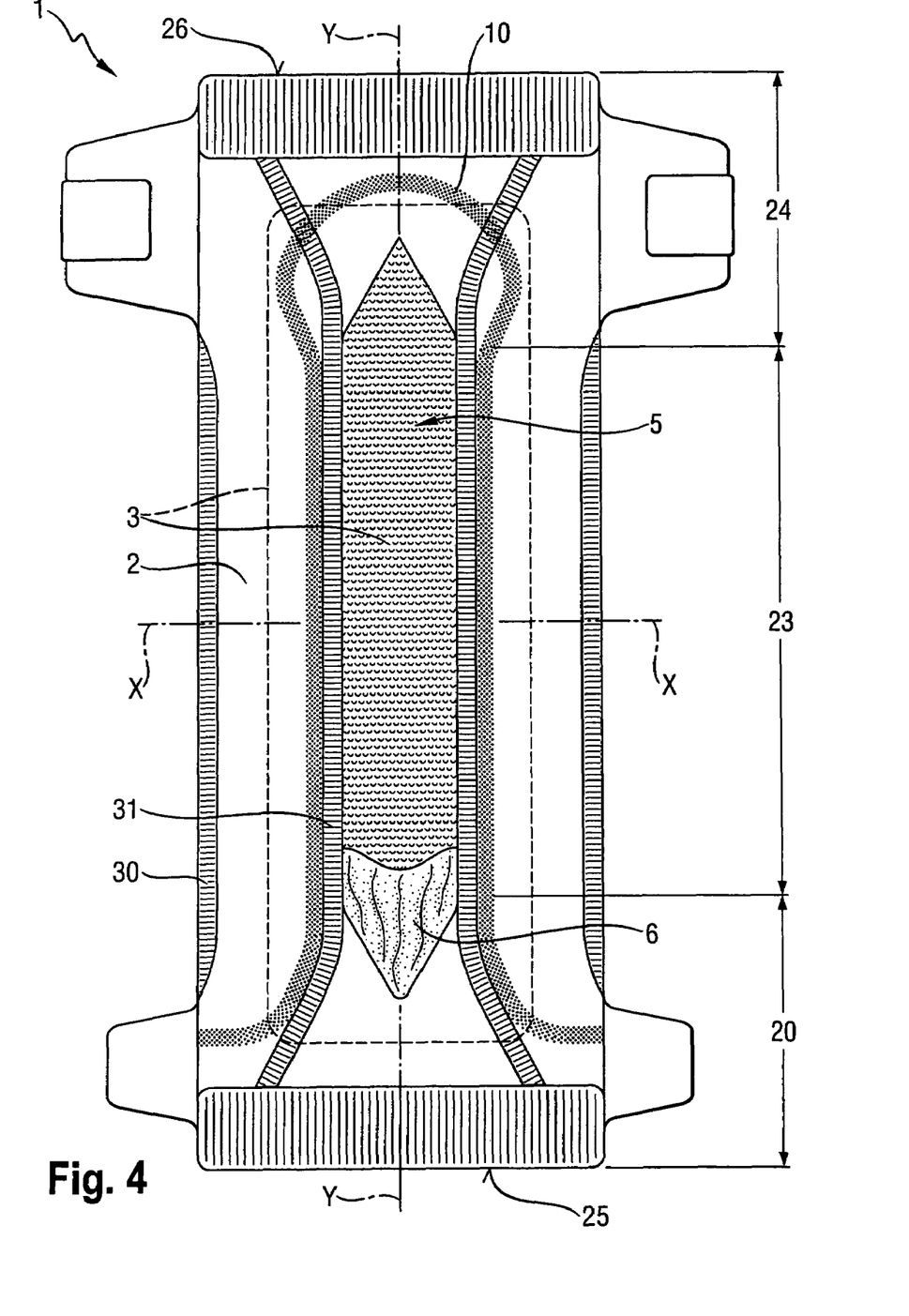
FIG. 4 shows a top view of the diaper of FIG. 2 of the kit of the invention in fully stretched state.

As shown for example in FIG. 4, the genital cover sheet may have a substantially transverse edge above, in or under the opening (5) which is not straight, but curved or V-shaped (arrow shaped), having the centre point of the curved edge or of the V-shaped edge closer to the front of the article (1) than the remaining part of the curved edge or V-shaped edge. Then, the length of the part of the genital coversheet (6) from this centre point to the front of the opening (5) may be about 10% to about 30% of the maximum length of the opening (5), about 15% to about 25%, or even to about 20%.

In another embodiment the article (1) may have at least two cuffs and a genital coversheet (6) attached to or placed over said cuffs, and covering part of the underlying core (3) in the front region (20) of the article (1).

In the first embodiment above, when the genital coversheet (6) is present under the topsheet (2) and below the opening (5) in the topsheet (2), and thus between the topsheet (2) and the absorbent core (3), then, the genital coversheet (6) may not be attached to the layer underneath, for example the absorbent core (3), to ensure the creation of a maximum void space for fecal material between the topsheet (2) and the absorbent core (3) and between the genital coversheet (6) and the absorbent core (3).

In one embodiment, the genital coversheet (6) may be extendable, either longitudinally or transversely or both, so that the pressure of the genitals onto the genital coversheet (6) causes the genital coversheet (6) to extend and form a pocket around the genitals. The genital coversheet (6) may be elastically extendable, or the genital coversheet (6) may be nonelastically extendable, in longitudinal and/or in transverse direction.

In another embodiment, the genital coversheet (6) may be an integral part of the topsheet (2) and it may form a pocket in the front of the article (1), to receive the genitals. This integral genital coversheet (6) is then typically urine permeable and/or hydrophilic, whilst the remaining portion of the topsheet (2), not forming a pocket for the genitals, may be urine impermeable and/or hydrophobic.

The primary serviceable indicium (10) may be applied to the component of the article (1) that is stretchable, but it may also or alternatively be applied to a non-stretchable component of the article (1). For example if the article (1) comprises a stretchable topsheet (2) and/or stretchable cuffs, the primary serviceable indicium (9) may be applied to the non-stretchable core or backsheet. It may be applied to a surface such that in use or during application it is visible for the user or caregiver. It may be applied or partially applied to the portion of the elasticated component where the elastic material (e.g. bands, strands) are present, or even on the elastic material.

In an embodiment, where the article (1) may comprise an elasticated topsheet (2) with at least one opening, the elastic material in the topsheet (2) herein may be in the form of at least one pair of elastic bands or strands, one on either longitudinal side of said opening (5) of the topsheet (2), and extending from said longitudinal side edges (31) of the opening(s) towards or to the front edge (25) and/or back edge (26) of the topsheet (2). Thus, the elastic bands or strands may be longer than the opening (5). The front end portions of two opposing primary elastics may bend away from one another (in the plane of the topsheet (2)), so that the distance between the end edges of the opposing front end portions of two opposing elastics may be larger that the distance between the centre portions of two opposing elastics, and equally, the distance between the end edges of the opposing back end portions of two opposing elastics may be larger that the distance between the centre portions of two opposing elastics. Then, each front end portion of an elastic band or strand may have an angle with a longitudinal line through the centre of the elastic band or strand and parallel to the longitudinal axis of the topsheet (2), said angle being from about 10° to about 40°, or from about 17° to about 35°, or from about 20° to about 35°. Then, the back end portion of each of elastic band or strand may have an angle with a longitudinal line through the centre of the elastic band or strand and parallel to the longitudinal axis of the topsheet (2), said angle being from about 10° to about 40°, or from about 17° to about 35°, or from about 20° to about 35°.

In one embodiment, the absorbent article (1) herein may have an elasticated topsheet (2) and it has a specific force profile as described in co-pending European application No 01117670.8, and as determined by the method set out therein. In one embodiment, the elasticated topsheet (2) of the article (1) may have an elastic profile, based on a two-cycle hysteresis, measured by the method set out in the co-pending application mentioned above, using a 500 mm/min clamp speed, which is as follows:

1.5 Lt by a first load force of less than 1.1N, 3.0 Lt by a first load force of less than 2.1N and 4.5 Lt by a first load force of less than 3.0N and a second unload force at 4.5 Lt of more than 0.9N, a second unload force at 3.0 Lt of more than 0.5 and a second unload force at 1.5 Lt of more than 0.1N.

In another embodiment, the elasticated topsheet may have an elastic profile as follows: 1.5 Lt by a first load force of less than 0.6 N, 3.0 Lt by a first load force of less than 1.1N and 4.5 Lt by a first load force of less than 1.5N and a second unload force at 4.5 Lt of more than 0.9N, a second unload force at 3.0 Lt of more than 0.5N and a second unload force at 1.5 Lt of more than 0.1N.

Profiles of an elasticated topsheet (2) herein are defined by the first load force and second load forces at all of the lengths in the following table (for a two cycle hysteresis with 500 mm/min clamp speed, stretching as set out below, up to 4.5 Lt or 0.8 $L_s$, which ever is smaller):

|  | Profile 1 | Profile 2 | Profile 3 |
|---|---|---|---|
| 1$^{st}$ load force at 1.5 Lt | <1.1 N | <1.1 N | <0.6 N |
| 1$^{st}$ load force at 2.0 Lt | <1.5 N | <1.5 N | <0.8 N |
| 1$^{st}$ load force at 2.5 Lt* | <1.8 N | <1.8 N | <0.9 N |
| 1$^{st}$ load force at 3.0 Lt* | <2.1 N | <2.1 N | <1.1 N |
| 1$^{st}$ load force at 3.5 Lt* | <2.3 N | <2.3 N | <1.2 N |
| 1$^{st}$ load force at 4.0 Lt* | <2.6 N | <2.6 N | <1.3 N |
| 1$^{st}$ load force at 4.5 Lt* | <3.0 N | <3.0 N | <1.5 N |
| 2$^{nd}$ unload force at 1.5 Lt | >0.1 N | >0.2 N | >0.1 N |
| 2$^{nd}$ unload force at 2. Lt | >0.3 N | >0.6 N | >0.3 N |
| 2$^{nd}$ unload force at 2.5 Lt* | >0.4 N | >0.8 N | >0.4 N |
| 2$^{nd}$ unload force at 3.0 Lt* | >0.5 N | >1.0 N | >0.5 N |
| 2$^{nd}$ unload force at 3.5 Lt* | >0.6 N | >1.2 N | >0.6 N |
| 2$^{nd}$ unload force at 4.0 Lt* | >0.7 N | >1.4 N | >0.7 N |
| 2$^{nd}$ unload force at 4.5 Lt* | >0.9 N | >1.8 N | >0.9 N |

*These values are only relevant as long as they are below 0.8 $L_{ts}$, as mentioned below in the test method.

In one embodiment, the article (1) may have a $L_c$ which is less than 0.5 $L_s$ of the article (1). $L_c$ of the article (1) may be less than 0.45 $L_s$ of the article (1), or even less than 0.4 $L_s$, or even less than 0.35 $L_s$, or even less than 0.3 $L_s$. Also other elasticated components, such as cuffs that extend over (part of) the length of the article (1) herein may have elastic profiles as described above.

Elastic materials used herein to make the elasticated components, such as the topsheets (2), of the articles (1) herein may include materials such as VFE-CD, available from Tredegar, and L-86, available from Fulflex (Limerick, Ireland), or L-89, also available from Fulflex. The elastic materials useful herein may for example have a thickness (e.g. gauge) of at least about 20 microns, at least about 40 microns, or at least about 60 microns, typically up to about 300 microns, or even up to about 200 microns or even up to about 150 microns. Materials may have a thickness of about 70 to about 100 microns.

The article (1) may be made by any known method. The elasticated component may also be made by any known method involving for example applying an elastic material in stretched state to a non-elastic material.

Topsheets (2) herein may be made of a sheet or sheets of hydrophobic material or a sheet, or sheet that are treated to be hydrophobic (in order to isolate the wearer's skin from liquids contained in remaining part of the diaper (1)), with for example a hydrophobic surface coating. Hydrophobic surface coatings are for example described in co-pending application U.S. 60/543,785, filed Feb. 11, 2004. The hydrophobic surface coating may comprise one or more silicone polymers or fluorinated polymers.

A suitable topsheet (2) may be manufactured from a wide range of materials, including woven or non-woven webs of natural fibers (e.g., wood or cotton fibers) or synthetic fibers (e.g., polyester, polyethylene and/or polypropylene fibers), or a combination of natural and synthetic fibers. If the topsheet (2) includes fibers, the fibers may be for example spun bond, carded, wet-laid, melt blown, hydro entangled, or otherwise processed as is known in the art. Webs may comprise spunbond layers (S) and meltblown layer(s) (M), wherein the surfaces of the web are formed by spunbond layer(s). Webs may have a relatively high basis weight, for example more than 25 gram/m (gsm), for example:

34 gsm SMMS (wherein 12 gsm meltblown and 5 gsm spunbond); 34 gsm SMMS (wherein 10 gsm meltblown and 7 gsm spunbond); 30 gsm SMMS (wherein 10 gsm meltblown and 5 gsm spunbond); 30 gsm SMMS (wherein 8 gsm meltblown and 7 gsm spunbond); 34 gsm SMS (wherein 20 gsm meltblown and 7 gsm spunbond), or for example webs comprising two layers of 17 gsm SMMS, described above.

Any portion of the topsheet (2) may be coated with a lotion or anti-friction powder, known in the art.

The absorbent article (1) may comprise an absorbent core (3), positioned under the topsheet (2) described above, or, if present, under a secondary topsheet, which may be an apertured sheet, such as an apertured (formed) film.

The absorbent article (1) also may comprise a typically liquid impervious backsheet (4), as known in the art. Suitable backsheet (4) materials may comprise breathable material, which permit vapors to escape from the diaper (1) while still preventing exudates from passing through the backsheet (4). Suitable backsheet (4) films include those manufactured by Tredegar Industries Inc. of Terre Haute, Ind. and sold under the trade names X15306, X10962 and X10964. The backsheet (4), or any portion thereof, may be elastically extendable in one or more directions.

The backsheet (4) may be attached or joined to the topsheet (2), secondary topsheet, the absorbent core (3), or any other element of the diaper (1) by any attachment means known in the art.

The attachment means to attach the topsheet (2) or secondary topsheet and the backsheet (4) may include for example pressure bonds or for example a uniform continuous layer of adhesive, a patterned layer of adhesive, or an array of separate lines, spirals, or spots of adhesive, such as disclosed in U.S. Pat. No. 4,573,986. Adhesives that have been found to be satisfactory are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

The absorbent core (3) may comprise any absorbent material which is generally compressible, conformable, non-irritating to the wearer's skin, and capable of absorbing and retaining urine, such as comminuted wood pulp, creped cellulose wadding; melt blown polymers, including coform; chemically stiffened, modified or cross-linked cellulosic fibers; tissue, including tissue wraps and tissue laminates; absorbent foams; absorbent sponges; super absorbent polymers; absorbent gelling materials; or any other known absorbent material or combinations of materials; absorbent cores (3) may have an absorbent storage layer which may comprise more than about 80% by weight of the absorbent core (3) content (e.g. excluding core (3) wrap, or coversheets) of absorbent gelling material, and which may comprise less than about 5%, or which is free of, absorbent cellulose fibers such as pulp.

The absorbent article (1) may also include a sub-layer disposed between the topsheet (2) or secondary topsheet and the absorbent core (3), capable of accepting, and/or immobilizing bodily exudates, typically fecal material. Suitable materials for use as the sub-layer may include large cell open foams, macro-porous compression resistant non woven highlofts, large size particulate forms of open and closed cell foams (macro and/or microporous), highloft non-wovens, polyolefin, polystyrene, polyurethane foams or particle, structures comprising a multiplicity of vertically oriented, looped, strands of fibers, or apertured formed films, as described above with respect to the genital coversheet (6). (As used herein, the term "microporous" refers to materials that are capable of transporting fluids by capillary action, but having a mean pore size of more than 50 microns. The term "macroporous" refers to materials having pores too large to effect capillary transport of fluid, generally having pores greater than 0.5 mm (mean) in diameter and more specifically, having pores greater than 1.0 mm (mean) in diameter, but typically less than 10 mm or even less than 6 mm (mean).

Kit (9) with Package (8) and Package (8)

Figure 5:
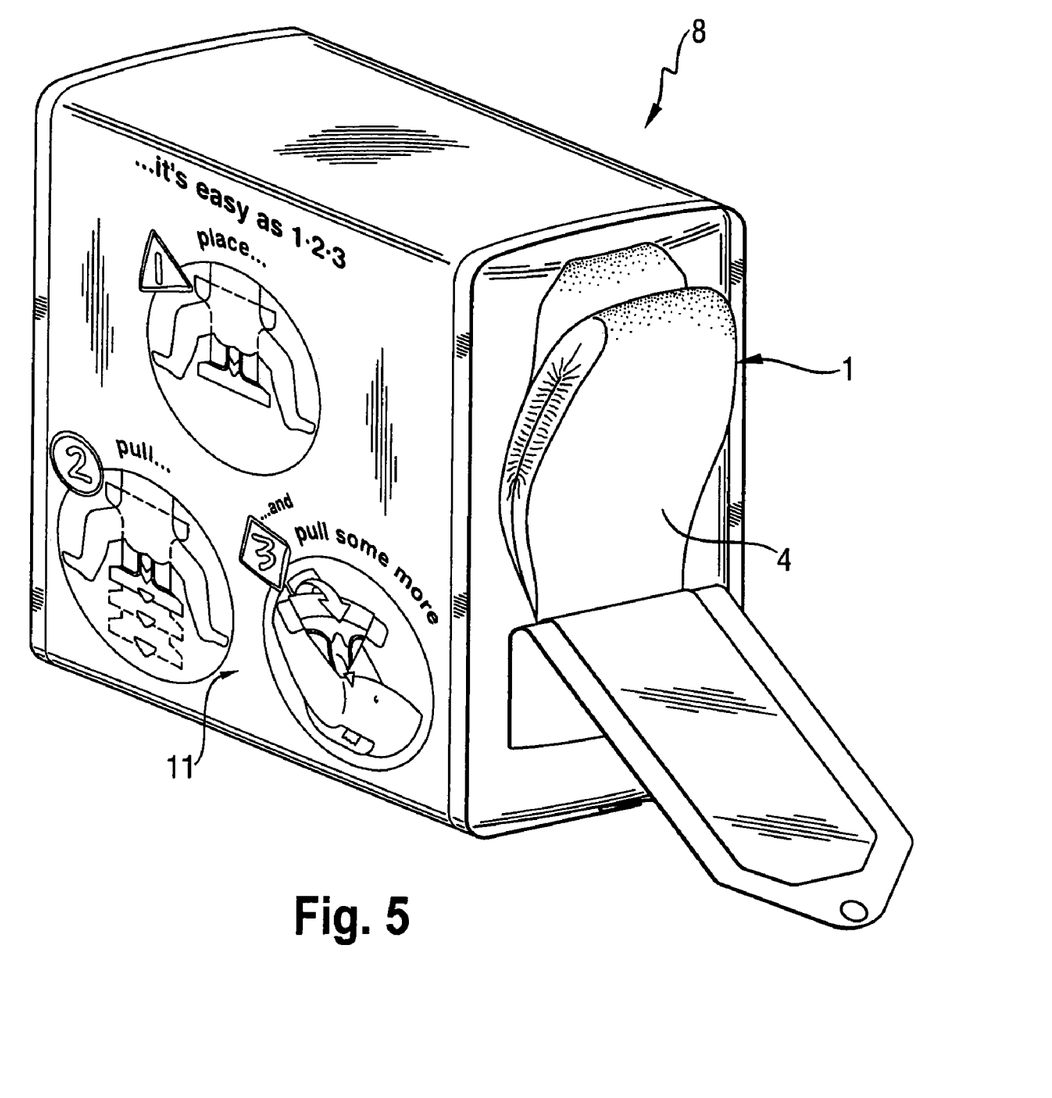
FIG. 5 shows a package or kit, comprising absorbent articles, and comprising the secondary information.

The package (8) herein may be any type of package (8) suitable to hold at least one disposable absorbent article (1) and typically a multitude of articles (1) (e.g., at least 10 articles). The package (8) may be made of a plastic or paper material that is wrapped or folded around said articles (1), as shown in FIG. 5. The package (8) may be a container that is at least partially or completely (excluding the closure) formed prior to addition of the articles, and it may have any form, for example a square or rectangular (cardboard) box. It may comprise an external surface which is visible to the caregiver or user. In one embodiment, the secondary information (11) described herein may be present on the external surface of the package (8), as shown in FIG. 5.

Figure 6:
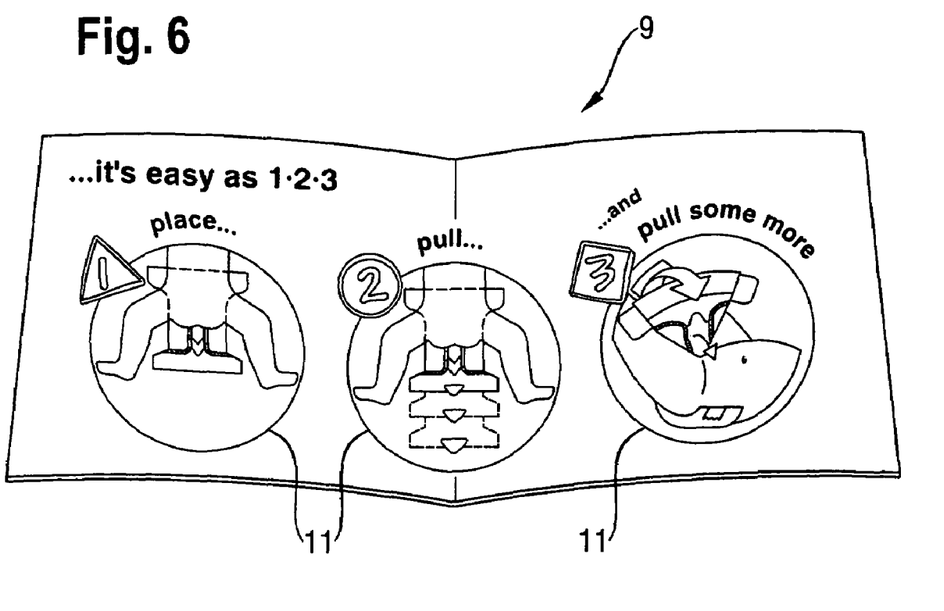
FIG. 6 shows a separate sheet with secondary information, useable in or with the package herein or in or with the package of the kit herein.

In another embodiment the package (8) may comprise an additional, separate means or item, for example a sheet, that is inserted in the package (8) or (removable) attached to the package (8), or provided with the package (8), and that may comprise said secondary information (11) described herein, such as for example the additional insert sheet shown in FIG. 6. The kit (9) herein may comprise a package (8) and at least one disposable absorbent article (1) comprised in said package (8), the package (8) and article (1) being as described above.

Primary Serviceable Indicium (10)

The absorbent article (1) herein may comprise at least one primary serviceable indicium (10) that conveys to the wearer (e.g. of a adult incontinence article (1)) or the caregiver (of a baby or infant, applying a diaper (1)):

i) that a pulling force is to be applied by the caretaker or wearer to the absorbent article (1) for correct application of the absorbent article (1) to the wearer, and typically in which direction the force needs to be applied (for example parallel to the force line of the forces of the elastic component, e.g. the elasticated topsheet); and/or ii) the correct alignment of the article (1) with the genitals and/or anus of the wearer.

In one embodiment the serviceable indicium (10) may be present on the component of the article (1) that is stretchable, e.g. elasticated, e.g. on a surface thereof that is visible prior to or during application of the article (1).

The serviceable indicium (10) may be any graphic, mark, symbol, pattern, or picture. The serviceable indium may be in the form of a contrasting indicium (10), being contrasting with the surrounding component that may comprise the indicium (10), for example having a contrasting color or texture. The serviceable indicium may be a colored indicium (10), for example applied to, e.g. printed onto, the article (1) (on one or more components of the article (1)). One or more contrasting lines on the stretchable components such as the cuffs or topsheet (2) described herein.

Figure 1:
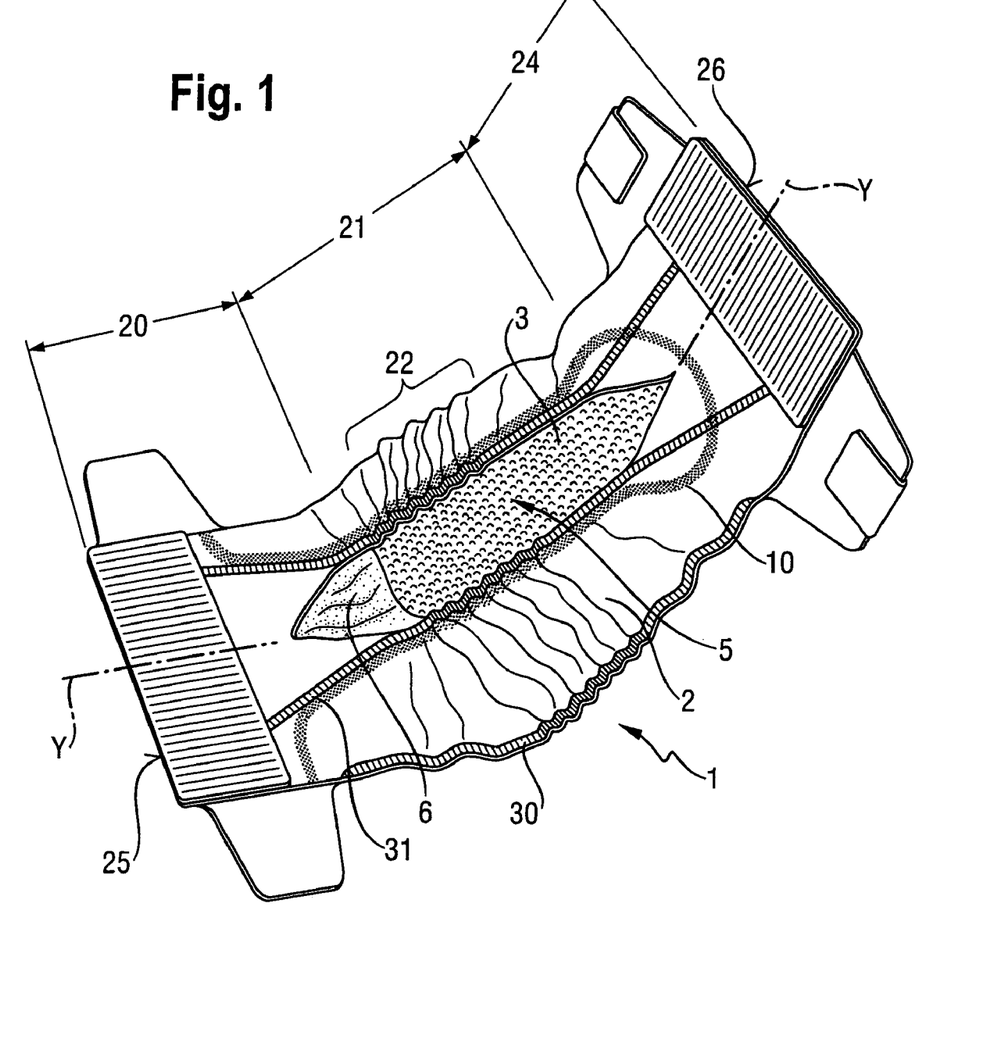
FIG. 1 shows a perspective view of a diaper of the kit of the invention.
Figure 2:
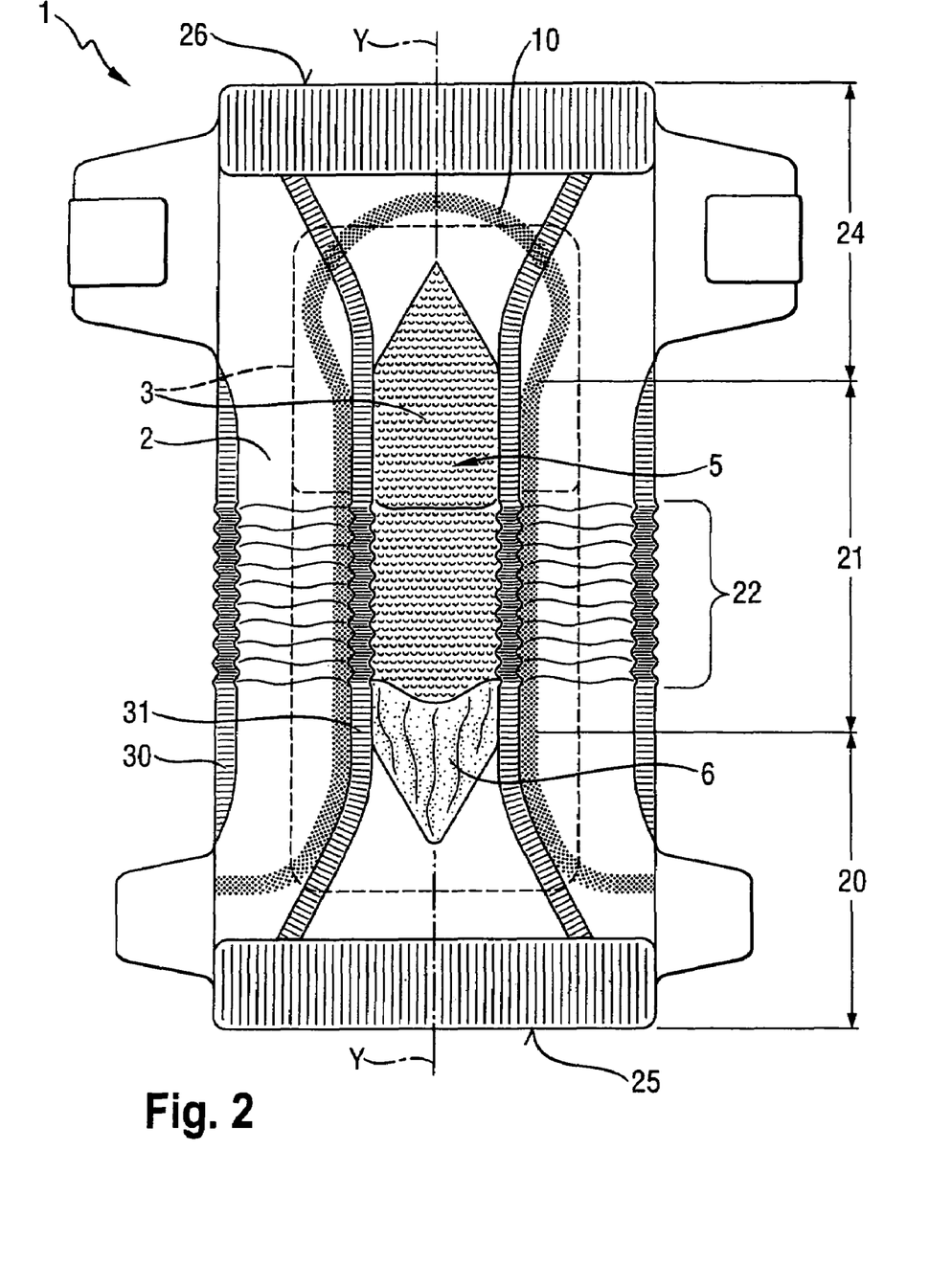
FIG. 2 shows a top view of a diaper of the kit of the invention is a partially contracted (i.e. partially stretched) flat state.
Figure 3:
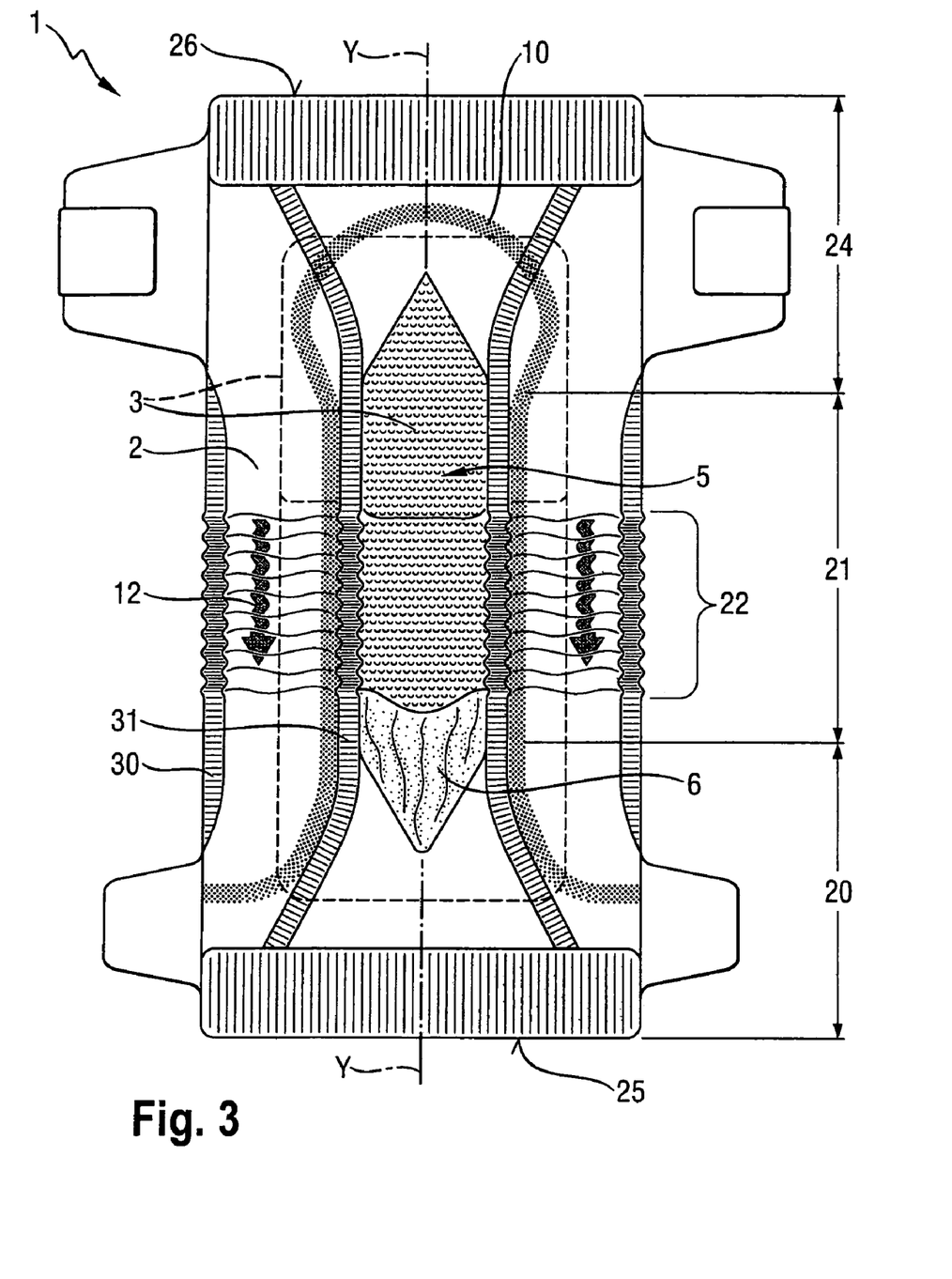
FIG. 3 shows a top view of another diaper of the kit of the invention comprising alternative primary serviceable indicium.

In one embodiment the absorbent article (1) may have a front region (20), centre region (21) and back region (24) (each having about 33.3% of the total length of the contracted absorbent article (1), laid flat on its backsheet on a surface) and it may comprise in said front region (20) one or more serviceable indicia that convey to the wearer or caregiver that a pulling force is to be applied along about the longitudinal direction, by for example comprising one or more lines, parallel with the force lines of the force caregiver or wearer should apply. For example, the serviceable indicium (10) or indicia may comprise one or more lines and/or arrows that are at least present in the front region (20) and that extend or point to or towards the front edge (25) of the article (1), or partially towards the front edge (25) and partially towards the side edge (30) of the article (1), as shown in FIGS. 3 and 4, indicating the direction of the pulling force to be applied.

In one embodiment, the serviceable indicium (10) may convey to the wearer or caregiver how to position the user (wearer, e.g. baby) such that correct application is achieved, e.g. that correct alignment of the anus and/or genitals are achieved. Thereto, the topsheet (2) and/or secondary topsheet may have serviceable indicium (10) to aid where to place the buttocks of the wearer and/or where to place the genitals, and/or to aid alignment of the buttocks or genitals with the article, e.g. with said opening (5) that may be present in the topsheet (2). This latter indicium may be part of the indicium described above indicating the application of pulling force, or it may be a separate indicium.

The article (1) may comprise, for example, a topsheet (2) with one or more openings, typically one, and with along each longitudinal side of said opening(s), and extending in at least substantially longitudinal direction, opposing elastic bands or strands, and comprising a serviceable indicium (10) such as a contrasting line around or along part of the opening (5) in the back region (24) and along the longitudinal edges (31) of the opening (5) and extending towards the front edge (25) of the article (1), to indicate the direction of the required force to be applied and to show the opening (5) or openings, so they can be aligned with the genitals and/or anus, as can be seen in for example FIGS. 1-4. The serviceable indicium (10) may even comprise one or more arrows to indicate the direction of force, as shown for example in FIG. 3. The serviceable indicium (10) may also comprise contrasting colour marks or graphics around the opening (5) or part thereof to better show the longitudinal edges (31) of the opening (5), and/or the underlying secondary topsheet (2) or core (3) under the opening (5) may comprise a (further) contrasting color to indicate the opening (5).

Secondary Information (11)

The package (8) herein may comprise secondary information (11) that may comprise a picture (including drawings or photo's) or graphic of the article (1) herein, or part thereof, and showing the primary serviceable indicium (10), or part thereof, and additional information (11) conveying to the caregiver or user how to interpret the primary serviceable indicium (10) and how to apply the article (1) correctly, for optimal performance, i.e. how to align the article with the anus/genitals, how to apply a pulling force. It may comprise two or more such pictures or graphics, and in addition symbols or text to convey said information. It also may comprise a picture of how the user (baby) is positioned in relation to the primary serviceable indicium (10), as shown in FIGS. 5 and 6.

The secondary information may convey to the caregiver:
i) to pull the absorbent article (1) to partially or fully stretched state; and prior to, simultaneous with or subsequent to step i)
ii) to place a baby or infant on the topsheet (2) of said article (1) or stretched article (1) in correct alignment;
and subsequently to ii) or i)
iii) to place the front region (20) of the diaper (1) over part of the belly of the baby of infant and fasten the article (1).

The secondary information may convey to the caregiver:
i) to pull the absorbent article (1) to partially or fully stretched state; and prior to, simultaneous with or subsequent to step i);
ii) to place a baby or infant on the topsheet (2) of said article (1) or stretched article (1) in correct alignment with the primary serviceable indicum (10) on the article;
ii) to pull the article (1) further over the belly of the baby or infant to fully stretched state;
iv) closing the fastening elements while keeping the article (1) in fully stretched state.

The secondary information (11) may be comprised by the package by any means, including on the external surface of the package, and/or on the internal surface of the package, and/or attached to the outside or inside of the package as additional component and/or inside the package as separate component, such components including information sheet(s)—including hologram sheets, sticker(s)—electronic components, such as a DVD, CD, video tape, comprising said information (11), or combinations of the possibilities above.

The secondary information (11) may be illustrated, e.g. printed on, an external surface of the package (8), as shown in FIG. 5. In addition, or alternatively, the secondary information (11) can be comprised by a sheet that is comprised inside the package (8) or attached to the package (8), and that may be removable attached, for example an insert cart in the package (8), as shown in FIG. 6.

In another embodiments, the secondary information (11) may not be comprised by the package (8) of the articles (1), but rather, may be provided as a separate information component or item to the caregiver or user, for example as information sheet, electronic information items supplied in the shop to the user or care giver when obtaining the articles (1). The kit may comprise one or more articles (1) as described herein and a separate secondary information component, obtainable with the purchase of one or more articles (1) herein. In each instances, the secondary information (11) may show the article (1) or part thereof and the primary serviceable indicium (10), or part thereof.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for accomplishing the application of a disposable absorbent article, having particular features, by a care giver to a wearer, comprising the step of providing a kit, the kit comprising:
   a) a package;
   b) a disposable absorbent article, comprising: a backsheet and a stretchable, elasticated topsheet, the topsheet comprising a longitudinal opening suitable to admit feces therethrough to a void space beneath said topsheet, said topsheet being elastically stretchable along a longitudinal direction, and at least one primary serviceable indicium disposed on said topsheet and conveying to the care giver;
      that a pulling force is to be applied to the absorbent article for correct application of the absorbent article to the wearer; or
      how to align the article with the genitals or anus of the wearer; or
      a combination thereof;
   wherein the package comprises secondary information that comprises:
      a depiction of the absorbent article and said primary serviceable indicium at least in part, and any of:
      instruction to the care giver to apply a pulling force to the absorbent article for correct application of the absorbent article to the wearer; or
      instruction to the care giver how to align the absorbent article with the genitals or anus of the wearer; or
      a combination thereof.

2. The kit method of claim 1 wherein said package comprises an external surface comprising said secondary information, or an insert comprising said secondary information, or a combination thereof.

3. The kit method of claim 2 wherein said secondary information comprises pictures, words, symbols, or any combination thereof.

4. The kit method of claim 1 wherein said secondary information comprises a picture of the disposable absorbent article or part thereof, comprising at least one primary serviceable indicium, conveying to the care giver; that a pulling force is to be applied to the absorbent article for correct application of the absorbent article to the wearer; or how to align the article with the genitals or anus of the wearer; or a combination thereof.

5. The method of claim 1 wherein either of said primary serviceable indicium or said secondary information convey to the care giver the direction of the required application of said pulling force.

6. The method of claim 1 wherein said primary serviceable indicium comprises one or more contrasting lines or bands or symbols, that extend in a longitudinal direction over a portion of said the absorbent article, and wherein said secondary information informs the care giver to align the serviceable indicium with a part of the wearer's body and to apply a pulling force along a force line parallel to the longitudinal direction of said article.

7. The method of claim 1 wherein said primary serviceable indicium comprises one or more contrasting lines with a curvature, wherein said contrasting lines are colored.

8. The method of claim 1 wherein the topsheet has a transverse x-axis, longitudinal y-axis, transverse front edge, transverse back edge, longitudinal side edges, front region and back region, and wherein at least a part of said serviceable indicium is disposed on said front region and comprises a pair of lines that: are mirror images of one another across the y-axis; extend from the transverse x-axis towards or to the transverse front edge of the topsheet; and each bend toward a longitudinal side edge of the topsheet.

9. The method of claim 1 wherein said absorbent article comprises an absorbent core, and said longitudinal opening leads to a void space between said topsheet and said absorbent core, and portions of said primary serviceable indicium are disposed at least in part along said longitudinal opening and at least on part on said absorbent core.

10. The method of claim 1 wherein said secondary information comprises a picture of an infant, or part thereof, placed on the topsheet of a stretched-open disposable absorbent article comprising said primary serviceable indicium, or part thereof.

11. The method of claim 1 wherein said absorbent article has a front region, and wherein said secondary information comprises a series of pictures or graphics conveying to the caregiver:
   i) to pull the absorbent article to a partially or fully stretched state;
   and prior to, simultaneous with or subsequent to step i),
   ii) to place an infant on the topsheet in correct alignment; and subsequently to step ii) or step i),
   iii) to place the front region over part of the belly of the infant and fasten the article.

12. The method of claim 1 wherein said absorbent article has a front region and fastening elements, and wherein said secondary information comprises a series of pictures or graphics conveying to the care giver;
   i) to pull the absorbent article to a partially or fully stretched state;
   and prior to, simultaneous with or subsequent to step i),
   ii) to place an infant on the topsheet in correct alignment with the primary serviceable indicium on the article;
   iii) to pull the article further over the belly of the infant to a fully stretched state;
   iv) to close the fastening elements while keeping the article in the fully stretched state.

* * * * *